United States Patent [19]

Letton

[11] Patent Number: 4,713,447

[45] Date of Patent: Dec. 15, 1987

[54] PROCESS FOR PREPARING ALKYL GLYCOSIDES

[75] Inventor: James C. Letton, Forest Park, Ohio

[73] Assignee: The Procter & Gamble Company, Cincinnati, Ohio

[21] Appl. No.: 536,472

[22] Filed: Sep. 28, 1983

Related U.S. Application Data

[63] Continuation-in-part of Ser. No. 509,895, Jun. 30, 1983, abandoned.

[51] Int. Cl.$^4$ .................................................. C07G 3/00
[52] U.S. Cl. ..................................... 536/18.6; 536/4.1; 536/124
[58] Field of Search .................. 536/127, 124, 18.6, 536/4.1

[56] References Cited

U.S. PATENT DOCUMENTS 3,839,318 10/1974 Mansfield ........................... 536/18.6

FOREIGN PATENT DOCUMENTS 0132043 1/1985 European Pat. Off. ........... 536/18.6

OTHER PUBLICATIONS

The Dispensatory, 24th Edition, Na Ethoxide, pp. 1588-1589.

*Primary Examiner*—Alan Siegel
*Attorney, Agent, or Firm*—Ronald L. Hemingway; Richard C. Witte

[57] ABSTRACT

Improvement in the acid catalyzed process for preparing alkyl glycosides by reaction of an alcohol with a monosaccharide or source of monosaccharide moiety, the improvement residing in the use of certain organic bases to neutralize the catalyst at the end of the reaction.

13 Claims, No Drawings

PROCESS FOR PREPARING ALKYL GLYCOSIDES

CROSS-REFERENCE TO RELATED APPLICATON

This is a Continuation-in-Part of U.S. Ser. No. 509,895, Letton, filed June 30, 1983, now abandoned.

FIELD OF THE INVENTION

The invention pertains to the preparation of alkyl glycosides by the reaction of a ($C_1$–$C_{30}$) alcohol with a monosaccharide, or other source of monosaccharide moiety in the presence of an acid catalyst, followed by neutralizaton with a base.

BACKGROUND ART

U.S. Pat. No. 3,839,318, Mansfield, issued Oct. 1, 1974, discloses a process for preparing alkyl glycosides by direct, acid catalyzed reaction of a higher alcohol and a saccharide. The disclosed catalysts are mineral acids such as hydrochloric and sulfuric acid and an acid cation exchange resin. Neutralization of the catalyst at the end of the reaction is with sodium hydroxide.

U.S. Pat. No. 3,547,828, issued Dec. 17, 1970, discloses a process for preparing higher alkyl glycosides by first reacting a saccharide with a lower alcohol (e.g., butanol) in the presence of an acid catalyst to form the lower alkyl glycoside, which is then reacted with the higher alcohol to effect transacetylation thereby forming the higher alkyl glycoside. The acid catalysts disclosed are mineral acids (e.g., $H_2SO_4$, $HNO_3$) and organic acids such as p-toluene sulfonic acid and methane sulfonic acid. It is stated that in general any "Lewis acid" may be used. Sulfuric acid is indicated as preferred. Neutralization of the catalyst at the end of the reaction is with sodium hydroxide.

U.S. Pat. No. 3,598,865, Lew, issued Aug. 10, 1971, discloses preparation of higher alkyl glycosides by acid catalyzed reaction of a saccharide and a higher alcohol in the presence of a lower alcohol (designated as a "latent solvent"). The acids disclosed as suitable catalysts are sulfuric, hydrochloric, phosphoric and p-toluenesulfonic acids and boron trifluoride. Neutralization of the catalyst at the end of the reaction is with sodium hydroxide.

U.S. Pat. No. 3,219,656, Boettner, issued Nov. 23, 1965, discloses a process for preparing higher alkyl glycosides by reaction of a higher alcohol with a saccharide in the presence of a lower alcohol and a macroreticular sulfonic acid ion exchange resin. Neutralization of the finished reaction mix is with calcium hydroxide.

It is desirable that alkyl glycosides, particularly those intended for use as, for example, surfactants in consumer products, be essentially colorless, or at least have very low color content.

It is the object of the present invention to provide improved color in alkyl glycosides.

SUMMARY OF THE INVENTION

The present invention is directed to an improvement in the acid catalyzed process for preparing alkyl glycosides from saccharides and alcohols, the improvement residing in the use of certain organic bases to neutralize the catalyst at the end of the reaction.

DETAILED DESCRIPTION OF THE PREFERRED EMBODIMENTS

The present invention is a process for preparing $C_1$–$C_{30}$ alkyl glycosides, comprising reacting a monosaccharide (or a source of the monosaccharide moiety such as a material readily hydrolyzable to a monosaccharide), with a $C_1$–$C_{30}$ monohydric alcohol in the presence of an acid catalyst and neutralizing the acid catalyst with an organic base selected from organic bases of the formula $(RO)_nM$, wherein R is an alkyl or acyl group containing from 1 to about 30 carbon atoms, M is an alkali metal, alkaline earth metal or aluminum and n is 1 when M is alkali metal, 2 when M is alkaline earth metal, and 3 when M is aluminum.

The monohydric alcohols containing from 1 to 30 carbon atoms used in the present invention may be primary or secondary alcohols, straight or branched chain, saturated or unsaturated, alkyl or aralkyl alcohols, ether alcohols, cyclic alcohols, or heterocyclic alcohols. In general, these alcohols have minimal solvent power for the saccharide molecule. Illustrative examples of the monohydric alcohols which may be employed in the pressent invention are methyl alcohol, isopropyl alcohol, butyl alcohol, octyl alcohol, nonyl alcohol, decyl alcohol, dodecyl alcohol, tridecyl alcohol, tetradecyl alcohol, pentadecyl alcohol, hexadecyl alcohol, heptadecyl alcohol, octadecyl alcohol, eicosyl alcohol, pentacosyl alcohol, oleyl alcohol, isoborneol alcohol, hydroabietyl alcohol, phenoxyethanol, phenoxypolyethoxyethanol containing five ethoxy groups, 2-methyl, 7-ethyl, 4-undecanol, and the like. A preferred group of alcohols are those having the formula ROH wherein R represents an alkyl group having from 8 to 30 carbon atoms. A particularly preferred group of alcohols are those wherein R represents an alkyl radical having from 12 to 18 carbon atoms. The alkyls can be straight or branched chain.

The saccharides used as reactants in the process herein are monosaccharides which can be alkylated in the "1" position, also sometimes called "reducing monosaccharides." These include hexoses and pentoses. Typical examples of suitable monosaccharides include glucose, manose, galactose, talose, allose, altrose, idose, arabinose, xylose, ribose, lyxose, and the like. For reasons of convenience, availability and low cost, the preferred saccharide is glucose.

Instead of monosaccharides, per se, materials which are hydrolyzable to monosaccharides can also be used as reactants in the present process. These include syrups such as corn syrup and molasses. Also the glycosides of the short chain ($C_1$–$C_4$) alcohols, e.g., methyl glycosides and butyl glycosides can be used as reactants which provide the monosaccharide moiety for making glycosides of higher (e.g., $C_8$–$C_{30}$) alcohols. The preferred reactants are the monosaccharides, and the process will be described herein primarily in the context of using a monosaccharide, glucose, as the source of saccharide moeity in the reaction.

The amount of alcohol and monosaccharide employed in the process will generally be such that the molar ratio of alcohol to monosaccharide is from about 1:1 to about 7:1. Preferably the molar ratio is from about 1.5:1 to about 3:1.

All percentages and ratios set forth herein are "by weight" unless stated otherwise.

The acid catalyst used in the process herein may be any of those generally recognized in the art as being suitable for use in catalysis of the reaction between an alcohol and saccharide. Specific examples are sulfuric acid, hydrochloric acid, phosphoric acid, phosphorous acid, p-toluene sulfonic acid, boron trifluoride and sulfonic acid ion exchange resins. Sulfuric acid and p-toluene sulfonic acid are preferred catalysts. Another preferred type of acid catalyst is the acid form of an anionic surfactant.

Many commercially available anionic surfactants are described in *McCutcheon's Detergents and Emulsifiers*, North American Edition, MC Publishing Co. (1980), incorporated by reference herein.

Anionic surfactants are normally used in the form of their neutralized alkali metal, alkaline earth metal or amine salts. However, when used as catalysts in the process of the present invention, they are used in their unneutralized (i.e., acid) form.

Preferred acid form anionic synthetic surfactants for use herein are:

(a) Alkyl sulfates of the formula $$RO(C_2H_4O)_nSO_3H$$

wherein R is an alkyl group of from about 8 to about 22 (preferably 12 to 18) carbon atoms, and n is from 0 to about 6. Examples are the sulfuric acid esters of lauryl and myristic alcohols and the sulfuric acid ester of the reaction product of one mole of lauryl alcohol and three moles of ethylene oxide.

(b) Alkylbenzene sulfonates of the formula

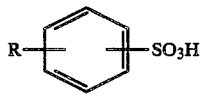

wherein R is alkyl of from about 8 to about 15, preferably about 12 to about 14, carbon atoms. Examples are decyl, dodecyl and tetradecyl benzene sulfonic acid.

(c) Alkyl sulfonates of the formula $$RSO_3H$$

wherein R is alkyl of from about 8 to about 22, preferably about 12 to about 18, carbon atoms. Examples are decyl, dodecyl and tetradecyl sulfonic acids.

The level of acid catalyst used in the process of the present invention is generally from about 0.0003 to about 0.016, preferably from 0.002 to about 0.006 moles per mole of saccharide.

The process herein is conducted at a temperature in the range of from about 100° C. to about 140° C. (preferably from about 100° C. to about 120° C., and most preferably about 105° C. to 112° C.). Water of reaction is removed as the reaction proceeds. This is most conveniently done by distillation.

Typically, the reaction is run by mixing the reactants and catalyst in a reaction vessel equipped with a distillation head for removing water of reaction. The reaction mixture is maintained at a temperature of from about 109° C. to about 112° C. and the progress of the reaction can be monitored by measurement of the amount of water removed and/or analysis of the unreacted monosaccharide content of the reaction mix. Preferably, the distillation is done under partial vacuum (e.g., 80–120 mm Hg) and a flow of nitrogen through the headspace. When the reaction is complete, the reaction mix is neutralized to pH about 6.6 to 7, preferably about 6.7 to 6.8, with base. Prior art practice has been to perform the neutralization with a conventional inorganic base such as alkali or alkaline earth hydroxides or alkali metal carbonate. In accordance with the present invention, it has been found that improved color (i.e., reduced formation of color bodies or color precursors which become visible upon further heating) is achieved if the catalyst is neutralized with an organic base of the formula $(RO)_nM$, wherein R is an alkyl or acyl radical of from 1 to about 30 carbon atoms, M is an alkali metal (i.e., a metal from Group IA of the periodic table of elements), an alkaline earth metal (i.e., a metal from Group IIA of the periodic table of elements) or aluminum, and n is 1 when M is alkali metal, 2 when M is alkaline earth metal, and 3 when M is aluminum. The terms "alkyl" and "acyl" as used herein include unsubstituted alkyl and acyl radicals, and the substituted alkyl and acyl radicals such as, for example, benzyl, haloalkyl, nitroalkyl, phenylacyl, haloacyl and the like. Preferred bases are those wherein R contains from 1 to about 4 carbon atoms. Examples of bases for use in the present invention are: sodium methoxide, sodium ethoxide, sodium 2-chloroethoxide, lithium ethoxide, sodium propoxide, potassium propoxide, sodium isopropoxide, sodium butoxide, sodium caproxide, sodium lauroxide, potassium palmitoxide, lithium stearoxide, sodium behenoxide, calcium diethoxide, magnesium diisopropoxide, barium dibutoxide, sodium formate, sodium acetate, sodium butyrate, sodium benzoate, potassium caprate, sodium laurate, potassium myristate, sodium stearate, sodium lignocerate, calcium diacetate, magnesium dibutyrate, calcium dipropionate, barium diacetate, aluminum triethoxide, aluminum triisopropoxide, aluminum tritertiarybutoxide, aluminum trilauroxide, aluminum triformate, aluminum triacetate, aluminum trilaurate and aluminum tristearate. As is known in the art, the bases in which R is an alkyl group and M is an alkali metal are made by reacting the corresponding alcohol (e.g., ethanol to make the ethoxide) with the alkali metal or its hydride. Bases in which R is alkyl and M is aluminum are made by reacting aluminum chloride with the alkali metal alkoxide of the corresponding alcohol (e.g., reacting one mole of aluminum chloride with three moles of sodium isopropoxide to make one mole of aluminum triisopropoxide) or by direct reaction of amalgamated aluminum with the alcohol. The bases in which R is acyl are salts of weak acids and are most conveniently made by neutralizing the acid with the alkali metal hydroxide or carbonate, alkaline earth metal hydroxide or aluminum hydroxide.

The alkaline earth metal alkoxides may be conveniently prepared by reacting the alkali metal oxide (e.g., CaO, MgO or BaO) with the corresponding alcohol. The calcium and magnesium alkoxides can also be made by direct reaction of the alkaline earth metal with the alcohol. Pertinent references are *Alcohols and Their Chemistry Properties and Manufacture*, by Monick, Rheinhold Book Corp., and *Chem. Abstracts*, 88:50268f and 84:124331n.

The amount of base used in the process of the present invention should be sufficient to achieve the target pH of from about 6.6 to 7.

This will generally be from about 1.0 to about 1.2 times the stoichiometric amount of acid catalyst employed. The base can be added to the reaction mix as a powder, but is preferably dissolved or dispersed in a solvent, such as ethanol.

After neutralization of the acid catalyst, it is usually desirable to distill the reaction mix to remove substantially all of the excess alcohol. This can be done, for example, in a thin film or wiped film evaporator, operated at about 160°-70° C. and about 0.5 mm pressure.

A typical procedure for carrying out the process of the invention is as follows. The reactor used is equipped with controlled heat source, vacuum source, nitrogen source, mechanical stirrer and distillation head.

Total Charge to the Reactor

1. Glucose (an amount suitable for the reactor size).
2. Higher alcohol (e.g., $C_{12}$–$C_{14}$) —2 moles per mole of glucose.
3. Acid catalyst—0.0056 mole per mole of glucose.
4. An organic base of the invention—to neutralize to pH about 6.7.
5. An organic solvent (e.g., ethanol)—sufficient to make a solution or slurry of the base.

Procedure

1. Glucose and higher alcohol are combined and homogenized. (If glucose monohydrate is used, the homogenized slurry is heated under vacuum to remove the water of hydration.)
2. Catalyst is added to the slurry and the temperature raised slowly to about 100° C.
3. The reaction mixture is then heated to 110° C., maintained at that temperature, and stirred at that temperature under a nitrogen atmosphere as water of reaction is removed from the reactor via a distillation head.
4. The reaction is continued until water ceases to be evolved.
5. A solution or slurry of base is added to the reaction mix until the pH of a 1% solution of the reaction mixture in water is at 6.7 to 6.8.
6. The neutralized crude product is centrifuged to remove insolubles and then stripped of excess higher alcohol by use of a wiped film evaporator.

Instead of introducing all of the monosaccharide and higher alcohol into the reaction vessel at the same time, the reaction can be conducted by incremental or continuous addition of monosaccharide to the higher alcohol at a controlled rate. This method of conducting the reaction tends to reduce the production of polysaccharide by-products. When incremental or continuous addition of monosaccharide is used, the rate of addition is preferably controlled such that the amount of unreacted monosaccharide in the reaction mix does not exceed 5 to 10% of the weight of the reaction mix at any given time, and the overall average amount of unreacted monosaccharide in the reaction mix over the course of the reaction should not exceed about 5% of the weight of the reaction mix. The amount of unreacted monosaccharide in the reaction mix can be monitored by gas chromatography of the trimethylsilyl derivative of the monosaccharide.

The use of organic base neutralization of catalyst in accordance with the present invention provides reduced level of colored by-products (and precursors of colored by-products which develop their color in the post-reaction alcohol stripping step).

The benefit of the present invention will be illustrated by the following example.

EXAMPLE 1

This example demonstrates the reduced color formation in alkyl glycosides attributable to use of base of the present invention to neutralize acid catalyst, as compared to the use of sodium hydroxide.

EXPERIMENTAL (a) One reaction was run and then divided into two equal weight portions for neutralization.
(b) The acid form of linear alkylbenzene sulfonate (HLAS) was the acid catalyst used.
(c) Anhydrous glucose (70 mesh) was added all at one time to the mixture of higher alcohol and catalyst at the beginning of the reaction.
(d) The reaction was run for three hours under a nitrogen flow in the headspace.
(e) The higher alcohol used was a $C_{12}$–$C_{14}$ blend.

Reaction Conditions—Description

Chemicals used:
 Glucose—100 gm (0.55 mole)
 $C_{12}$–$C_{14}$ Alcohol—214 gms (1.1 moles)
 HLAS—0.00315 mole
 Sodium Ethoxide—0.106 gm (0.00155 mole)
 Sodium Hydroxide—0.063 gm (0.00155 mole)

Procedure:

A one liter flask equipped with a distillation condenser, overhead stirrer, nitrogen inlet and thermometer was used. The reaction flask was heated by a heating mantle with the reaction temperature controlled by a thermo-watch.

The alcohol and acid catalyst were combined in the reactor after the alcohol had been heated alone to 110° C. to insure dryness. The acid catalyst-alcohol solution was cooled to 85° C. and 100 grams of anhydrous glucose were added.

The temperature was raised to 110° C. and the reaction continued with stirring under a nitrogen atmosphere for three hours. The temperature was held at 109°-112° C. throughout the reaction.

After three hours of reaction time, the reaction mixture was separated into two equal weight portions. One-half of the reaction mixture was neutralized by the addition of sodium hydroxide in water in an amount chemically equivalent to the amount of acid catalyst in one-half of the reaction mixture. The second half of the reaction mixture was neutralized by the addition of sodium ethoxide in ethanol in an amount equivalent to the amount of acid catalyst present in one-half of the reaction mixture.

The neutralized crude mixtures were sampled and these samples stripped by thin film evaporation at 130° C. and 2 mm Hg vacuum for one hour each to remove most of the excess $C_{12}$–$C_{14}$ alcohol.

The stripped samples (solids) were ground and 1 gm of each was weighed on an analytical balance. The alcohol-free samples were dissolved in 100 mls of 70/30 ethanol/water to make a 1% solution. 50 mls of each solution was again diluted to 100 mls with the same solvent to prepare a 0.5% solution.

The development of undesirable color in acid catalyzed monosaccharide reactions may be monitored by U.V.-VIS spectrophotometry. Known color precursors, such as furan derivatives and other unsaturated carbonyl compounds absorb in the range of 270 to 350 nm. Color bodies absorb at 400 to 500 nm. and above, particularly at 440 and 470 nm.

The 0.5% solutions prepared above were scanned by use of a recording spectrophotometer. The data are shown in Table 1.

TABLE 1

| | nm. | Absorbance Sodium Ethoxide | Sodium Hydroxide |
|---|---|---|---|
| Ultraviolet | 270 | 0.700 | 1.188 |
| | 300 | 0.4987 | 0.881 |
| | 330 | 0.3633 | 0.727 |
| Visible | 440 | 0.1492 | 0.3344 |
| | 470 | 0.1249 | 0.2766 |

These data show that the sodium ethoxide-neutralized reaction product had lower levels of color precursors and a lower level of color bodies, as compared to sodium hydroxide-neutralized reaction product.

What is claimed is:

1. An improved process for preparing alkyl glycosides having from about 1 to about 30 carbon atoms in the alkyl chain, comprising the steps of:
   (a) reacting a $C_1$ to $C_{30}$ monohydric alcohol with a source of reducing monosaccharide moiety, selected from the group consisting of reducing monosaccharides, corn syrup, molasses and the glycosides of $C_1$ to $C_4$ alcohols, in the presence of an acid catalyst; and
   (b) neutralizing the catalyst with a base to a pH of from about 6.6 to about 7;
the improvement comprising neutralizing the catalyst with an organic base of the formula $(RO)_nM$, wherein R is a substituted or unsubstituted alkyl or acyl of from 1 to about 30 carbon atoms, M is selected from the group consisting of alkali metal, alkaline earth metal and aluminum and n is 1 when M is alkali metal, 2 when M is alkaline earth metal, and 3 when M is aluminum.

2. The process of claim 1 wherein the R in the organic base is an unsubstituted alkyl or acyl radical of from 1 to about 4 carbon atoms.

3. The process of claim 2 wherein the monohydric alcohol contains from 8 to about 30 carbon atoms.

4. The process of claim 3 wherein the source of reducing monosaccharide moiety is a monosaccharide.

5. The process of claim 4 wherein the acid catalyst is selected from the group consisting of sulfuric acid, hydrochloric acid, phosphoric acid, phosphorous acid, p-toluene sulfonic acid, boron trifluoride, sulfonic acid ion exchange resins, and unneutralized anionic surfactants.

6. The process of claims 1, 2, 3 through 5 wherein R in the organic base is an unsubstituted alkyl radical of from 1 to about 4 carbon atoms.

7. The process of claim 6 wherein the acid catalyst is selected from the group consisting of:
   (a) Alkyl sulfates of the formula

wherein R is an alkyl group of from about 8 to about 22 carbon atoms, and n is from 0 to about 6,
   (b) Alkylbenzene sulfonates of the formula

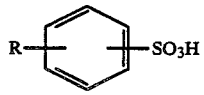

wherein R is alkyl of from about 8 to about 15 carbon atoms, and
   (c) Alkyl sulfonates of the formula

wherein R is alkyl of from about 8 to about 22 carbon atoms.

8. The process of claim 7 wherein the acid catalyst is an alkylbenzene sulfonic acid having from 12 to 14 carbon atoms in the alkyl chain and the neutralizing base is sodium ethoxide.

9. The process of claims 1, 2, 3 through 5 wherein R in the neutralizing base is an acyl radical of from 1 to about 4 carbon atoms.

10. The process of claim 9 wherein the acid catalyst is selected from the group consisting of:
    (a) Alkyl sulfates of the formula

wherein R is an alkyl group of from about 8 to about 22 carbon atoms, and n is from 0 to about 6,
    (b) Alkylbenzene sulfonates of the formula

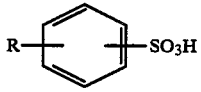

wherein R is alkyl of from about 8 to about 15 carbon atoms, and (c) Alkyl sulfonates of the formula

wherein R is alkyl of from about 8 to about 22 carbon atoms.

11. The process of claim 10 wherein the neutralizing base is sodium acetate.

12. The process of claim 4 wherein the source of reducing monosaccharide is glucose.

13. The process of claim 4 wherein the source of reducing monosaccharide is corn syrup.

* * * * *